United States Patent
Rosenberg et al.

(10) Patent No.: US 9,498,627 B2
(45) Date of Patent: Nov. 22, 2016

(54) WIRELESS CLOSED-LOOP AND SYSTEM TO DETECT AND TREAT SLEEP APNEA

(71) Applicant: PACESETTER, INC., Sylmar, CA (US)

(72) Inventors: Stuart Rosenberg, Castaic, CA (US); Melanie Goodman Keiser, McKinney, TX (US); Lalit Venkatesan, McKinney, TX (US); Didier Theret, Porter Ranch, CA (US)

(73) Assignee: PACESETTER, INC., Sylmar, CA (US)

( * ) Notice: Subject to any disclaimer, the term of this patent is extended or adjusted under 35 U.S.C. 154(b) by 152 days.

(21) Appl. No.: 14/156,181

(22) Filed: Jan. 15, 2014

(65) Prior Publication Data

US 2015/0196766 A1    Jul. 16, 2015

(51) Int. Cl.

| A61N 1/00 | (2006.01) |
|---|---|
| A61N 1/36 | (2006.01) |
| A61B 5/08 | (2006.01) |
| A61B 5/00 | (2006.01) |
| A61B 5/021 | (2006.01) |
| A61B 5/145 | (2006.01) |
| A61B 5/0215 | (2006.01) |
| A61B 5/053 | (2006.01) |

(52) U.S. Cl.
CPC ........... *A61N 1/36139* (2013.01); *A61B 5/021* (2013.01); *A61B 5/0826* (2013.01); *A61B 5/14542* (2013.01); *A61B 5/4818* (2013.01); *A61B 5/4836* (2013.01); *A61N 1/3601* (2013.01); *A61N 1/3611* (2013.01); *A61B 5/0215* (2013.01); *A61B 5/0533* (2013.01); *A61B 5/682* (2013.01); *A61B 2505/07* (2013.01)

(58) Field of Classification Search
CPC .......................... A61N 1/3601; A61N 1/3611
USPC .......................................................... 607/42
See application file for complete search history.

(56) References Cited

U.S. PATENT DOCUMENTS

| 6,240,316 B1 | 5/2001 | Richmond et al. |
|---|---|---|
| 6,345,202 B2 | 2/2002 | Richmond et al. |
| 7,650,189 B1 | 1/2010 | Park et al. |
| 7,942,822 B1 | 5/2011 | Koh |
| 8,260,432 B2 | 9/2012 | DiGiore et al. |
| 8,428,746 B2 | 4/2013 | DiGiore et al. |
| 8,457,757 B2 | 6/2013 | Cauller et al. |
| 2001/0010010 A1 | 7/2001 | Richmond et al. |

(Continued)

*Primary Examiner* — Amanda Patton
*Assistant Examiner* — Philip C Edwards

(57) ABSTRACT

A wireless implantable system is provided that is externally powered and comprises of a closed-loop feedback for treating both patients with obstructive and central sleep apnea. A method is provided for treating sleep apnea using an implantable device. The method comprises sensing an inspiration (IN) signal representative of inspiration experienced by a patient from a respiratory surrogate signal and sensing a respiratory effort (RE) signal representative of an amount of effort exerted by the patient during respiration. The method also comprises analyzing the inspiration signal relative to an IN baseline, that corresponds to normal respiratory behavior, to identify an IN indicator, analyzing the RE signal relative to an RE baseline, that corresponds to a normal amount of respiratory exerted by the patient, to identify an RE indicator, declaring a central sleep apnea (CSA) state or an obstructive sleep apnea (OSA) state based on the IN and RE indicators, and delivering at least one of a CSA therapy when the CSA state is declared or an OSA therapy when the OSA state is declared.

24 Claims, 9 Drawing Sheets

(56) References Cited

U.S. PATENT DOCUMENTS

| | | |
|---|---|---|
| 2005/0215847 A1* | 9/2005 | Heruth et al. .................. 600/26 |
| 2008/0109046 A1 | 5/2008 | Lima et al. |
| 2010/0331920 A1 | 12/2010 | DiGiore et al. |
| 2011/0172733 A1 | 7/2011 | Lima et al. |
| 2012/0029362 A1* | 2/2012 | Patangay et al. ............. 600/484 |
| 2013/0046361 A1 | 2/2013 | DiGiore et al. |

\* cited by examiner

WIRELESS CLOSED-LOOP AND SYSTEM TO DETECT AND TREAT SLEEP APNEA

BACKGROUND OF THE INVENTION

Embodiments of the present invention generally relate to methods and systems for treating sleep apnea.

Sleep apnea is a common condition with serious consequences adversely affecting quality of life and overall health. It is comorbid with a number of other diseases including heart failure and obesity, and has been linked to increased risk of poor outcomes. A common treatment for sleep apnea is a Continuous Positive Airway Pressure (CPAP) device, which may provide benefit but with great inconvenience for the patient and for the patient's partner. Obstructive sleep apnea is the most common type of sleep apnea and is caused by the relaxation of the posterior tongue muscles that result in obstruction of the upper airways. Some surgical options exist for extreme cases, and several implantable devices seek to treat apnea, including hypoglossal nerve stimulation. Hyperglossal nerve stimulation results in the contraction of the posterior tongue muscles, and as a result, advances the tongue and unblocks the airway. This neurostimulation technique improves snoring, but is ineffective in the treatment of central sleep apnea.

However, conventional approaches for apnea treatment continue to have areas for improvement. For example, conventional systems generally utilize a mask, placed over the patient's face during sleep, to directly measure (and/or control) air entering and leaving the patient's airway passage. Wearing a mask during sleep is not desirable.

Also, conventional apnea stimulation treatment devices are battery powered. The batteries have a limited life cycle before requiring the device to be explanted. The useful life of the device battery varies with a size of the battery. Thus, a longer duration battery is relatively larger which in turn increases the size of the overall device.

Further, conventional stimulation systems treat apnea events generally, in that all types of apnea experienced by a patient receive a common stimulation therapy. However, different types of apnea events respond better to different types of therapy.

A need remains for methods and systems that are able to monitor for apnea episodes without directly interfering with the patient's airway passage. Also, a need remains for methods and systems that are able to discriminate between and selectively treat different types of sleep apnea events.

Further, a need remains for an implantable device for treating apnea, where the device life cycle and size are not dependent on batteries within the device.

SUMMARY

In accordance with one embodiment, a wireless implantable system is provided that is externally powered and comprises of a closed-loop feedback for treating both patients with obstructive and central sleep apnea. In accordance with an embodiment, a method is provided for treating sleep apnea using an implantable device. The method comprises sensing an inspiration (IN) signal representative of inspiration experienced by a patient from a respiratory surrogate signal and sensing a respiratory effort (RE) signal representative of an amount of effort exerted by the patient during respiration. The method also comprises analyzing the inspiration signal relative to an IN baseline, that corresponds to normal respiratory behavior, to identify an IN indicator, analyzing the RE signal relative to an RE baseline, that corresponds to a normal amount of respiratory exerted by the patient, to identify an RE indicator, declaring a central sleep apnea (CSA) state or an obstructive sleep apnea (OSA) state based on the IN and RE indicators, and delivering at least one of a CSA therapy when the CSA state is declared or an OSA therapy when the OSA state is declared.

Optionally, the method may include delivering at least one of a nerve stimulation or a muscle stimulation configured to induce breathing. As another option, the method may include CSA therapy that includes targeting nerve stimulation at a phrenic nerve when the declaring declares the CSA state. Optionally, the method may include OSA therapy that includes targeting nerve stimulation at a hypoglossal nerve when the declaring declares the OSA state. As another option, the method may include CSA therapy that includes targeting muscle stimulation at a diaphragm when the declaring declares the CSA state. Alternatively, the method may include OSA therapy that includes targeting muscle stimulation at oropharyngeal muscles when the declaring declares the OSA state.

Optionally, the method may include sensing at least one of a blood pressure or a blood oxygen saturation as an indirect measure of respiration. As another option, the method may be configured wherein the therapy is delivered upon detection of a change or cessation of respiratory-related blood pressure oscillations in a pulmonary artery. Alternatively, the therapy may be delivered upon detection of reduced oxygen saturation in a pulmonary arterial blood or superior vena cava. Optionally, the sensing comprises receiving a surrogate pulmonary artery blood pressure (PABP) signal that changes over respiratory cycles, the surrogate PABP signal including an indication of a magnitude and a period of the inspiration. Optionally, the sensing further comprises low pass filtering the PABP signal with a cutoff at a predefined frequency to generate a low pass filtered PABP signal that increases and decreases in magnitude in accordance with changes in inspiration over a respiratory cycle.

In accordance with an embodiment, a system is provided for treating sleep apnea. The system comprises sensors configured to sense inspiration and output an inspiration (IN) signal, representative of inspiration experienced by a patient, as a respiratory surrogate signal, the sensors configured to sense a respiratory effort (RE) and output an RE signal representative of an amount of effort exerted by the patient during respiration. The system also comprises an analysis circuit module configured to analyze the IN signals relative to an IN baseline, that corresponds to normal respiratory behavior, to identify an IN indicator. The system includes the analysis circuit module configured to analyze the RE signal relative to an RE baseline, that corresponds to a normal amount of respiratory effort exerted by the patient, to identify an RE indicator. The system also includes a therapy circuit module configured to declare a central sleep apnea (CSA) state or an obstructive sleep apnea (OSA) state based on the IN and RE indicators; and an implantable device configured to deliver at least one of a CSA therapy when the CSA state is declared or an OSA therapy when the OSA state is declared.

Optionally, the system may be configured wherein the implantable device includes a lead positioned proximate to nerves or muscle of interest, the lead having electrode configured to deliver at least one of a nerve stimulation or a muscle stimulation configured to induce breathing. Alternatively, the system may be configured wherein the therapy circuit module targets nerve stimulation at a phrenic nerve when the declaring declares the CSA state. Optionally the system may include the therapy circuit module targeting nerve stimulation at a hypoglossal nerve when the declaring declares the OSA state. As another option, the system may be configured wherein the therapy circuit module targets muscle stimulation at a diaphragm when the declaring declares the CSA state.

As another option, the system may include the therapy circuit module targeting muscle stimulation at oropharyngeal muscles when the declaring declares the OSA state. Optionally, the system may be configured wherein the sensors further comprise at least one of an implantable blood pressure sensor or an implantable blood oxygen saturation sensor configured to generate the IN signal as the respiratory surrogate signal.

Alternatively, the system may be configured wherein the sensors include a pulmonary pressure sensor configured to output a pulmonary artery blood pressure (PABP) signal as the IN signal, further comprising a low pass filter configured to remove a high frequency component from the PABP signal to produce a lowpass PABP signal as the IN signal. As another option, the analysis circuit module may be configured to receive, as the IN signal, a surrogate pulmonary artery blood pressure (PABP) signal that changes over respiratory cycles, the analysis circuit module configured to declare the CSA state or OSA state when at least one of a peak to peak magnitude or a period of the inspiration fails to satisfy at least one of a predetermined inspiration magnitude or period thresholds. Optionally, the sensors further comprise a galvanic sensor configured to sense the RE signal representative of the amount of effort exerted by the patient during respiration.

Optionally, the system may further comprise an external device that includes the analysis and therapy circuit modules, the external device having inputs configured to receive the IN and RE signals from the sensors, the external device coupled to an antenna configured to communicate with the implantable device. Alternatively, the system may further comprise an external device that includes the analysis and therapy circuit modules, wherein the sensors are implantable in the patient, the external device coupled to an antenna configured to communicate with the sensors to receive at least one of the IN or RE signals. As another option, the system may further comprise first and second antenna configured to be located in a bed or pillow of the patient proximate to a torso and head of the patient.

DETAILED DESCRIPTION

System Overview

Figure 1A:
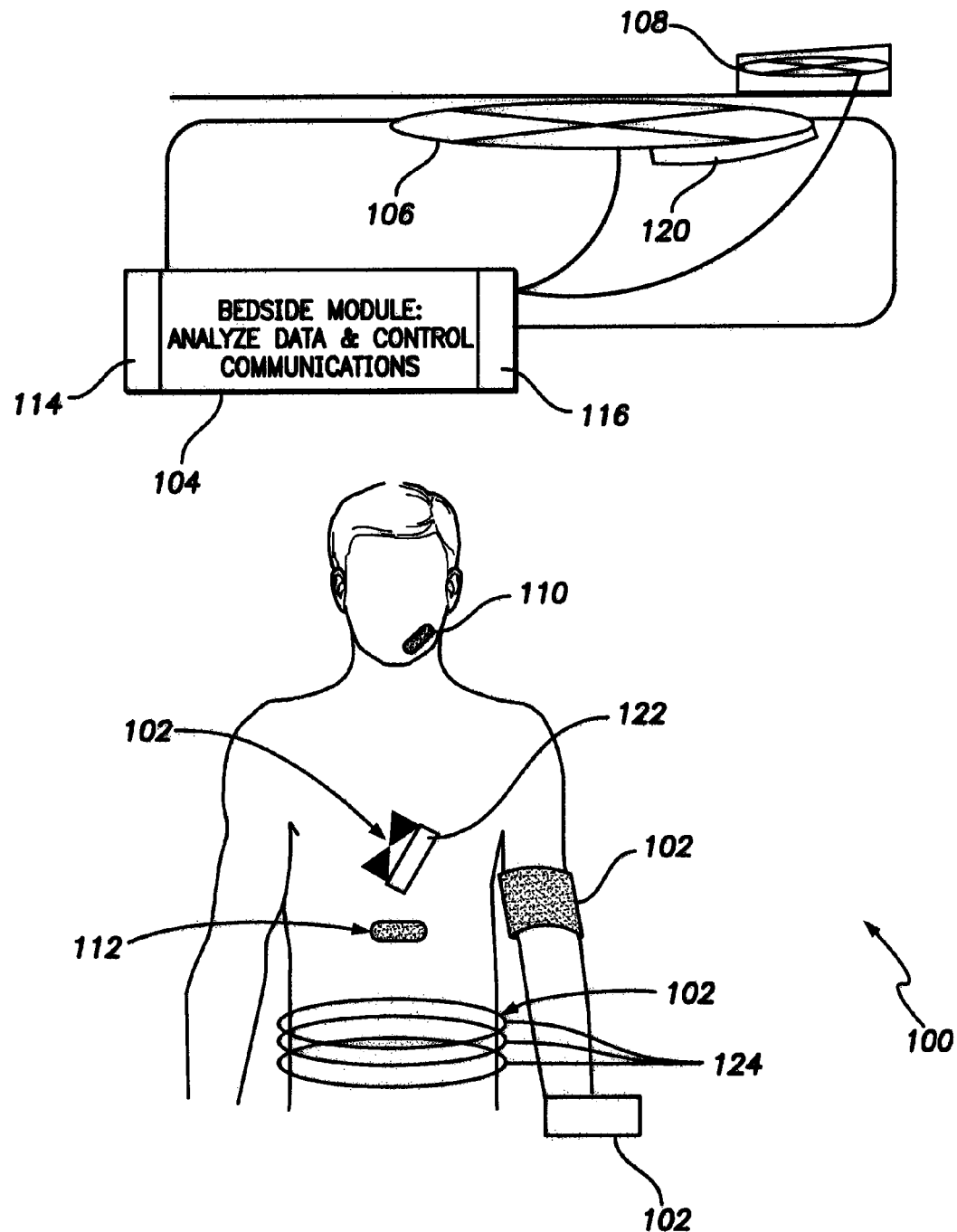
FIG. 1A, formed in accordance with an embodiment, illustrates a system for detecting and treating sleep apnea.

FIG. 1 illustrates a system 100 for detecting and treating sleep apnea. The system 100 includes one or more sensors 102 that are configured to be implanted into the patient or placed against or proximate the patient's skin.

The system 100 includes one or more stimulation devices 110 and 112, one or more of which may represent an implantable device. One or more of the devices 110 and 112 are configured to deliver central sleep apnea (CSA) therapy when a CSA state is declared and/or an obstructive sleep apnea (OSA) therapy when an OSA state is declared. Optionally, the stimulation devices 110, 112 may include an implantable device having a lead positioned proximate to nerves or muscles of interest. The lead has one or more electrodes that are configured to deliver at least one of a nerve stimulation or a muscle stimulation that is configured to induce breathing. The stimulation devices 110, 112 may be implemented through a "capsule" that receives energy or power from an external device and stimulates tissue nearby an implanted electrode location. The "capsule" (e.g., housing) of the stimulation device(s) 110, 112 may be relatively small, such as a size of the two quarters, a volume generally of 35-50 ml, a volume more preferably of 5-20 ml and the like. For example, the electrodes may be positioned near the tongue muscles or hypoglossal nerve in patients with obstructive sleep apnea or near the phrenic nerve or diaphragm in patients with central sleep apnea.

The sensors 102 are configured to indirectly sense inspiration experienced by the patient during successive, numerous respirator cycles. The sensors 102 output inspiration (IN) signals that vary over time representative of inspiration and expiration over the respirator cycle. The IN signals output by at least one of the sensors 102 represent respiratory surrogate signals in that the sensors 102 do not directly measure air flow from a patient airway. Instead, at least one of the sensors 102 measures one or more physiologic characteristics that vary in a known or predicted manner with respiration and are indicative of inspiration and respiration.

The sensors 102 also include at least one sensor that is configured to measure a physiologic characteristic indicative of a respiratory effort (RE) that is experienced by the patient during respiration. The sensor(s) 102, that sense surrogates for respiratory effort, output an RE signal representative of an amount of effort exerted by the patient during respiration over one or numerous respiration cycles. The sensors 102 may be coupled through wires or wirelessly with an implantable device and/or an external device (e.g., a bedside monitor) to deliver analog or digital IN and RE signals, explained in more detail below.

The sensors 102 may comprise at least one of an implantable blood pressure sensor and/or an implantable blood oxygen saturation sensor that are configured to generate the IN signals as the respiratory surrogate signals. Optionally, the sensors 102 may include a pressure sensor located in the pulmonary artery that outputs a pulmonary arterial pressure signal that includes an inspiration signal component. The sensor 102 or external device 104 may include a low pass filter configured to remove a high frequency component from the pulmonary arterial pressure signal to produce a low pass filtered PABP signal as the inspiration signal.

The sensor 102 may sense respiration changes the baseline pulmonary artery blood pressure (PABP). A baseline or low frequency (~2-20 per minute/0.033-0.33 Hz) content of the blood pressure measurement is related largely to changes in thoracic pressure with respiration. In one embodiment, a low-pass filtered PABP signal with cutoff around 0.5 Hz can be used as a surrogate for respiration. The period and peak to peak amplitude at the low pass filtered PABP signal are analyzed When the PABP signal flattens (e.g., small peak to peak amplitude) for a period of several seconds, a possible apneic event is indicated. In another embodiment, a wider bandwidth signal such as DC—10 Hz may be used in conjunction with a nadir detector or peak detector can be used as a surrogate for respiration. When a string of approximately 6 successive nadirs or successive peaks vary by less than a predetermined threshold, a possible apneic event is indicated.

Optionally, the sensor 102 may monitor other aspects of blood pressure that also modulate with respiration. The sensor 102 may measure pressure from various thoracic vessels and in particular from the superior or inferior vena cava, or also from the right atrium, right ventricle, or left atrium. The sensor 102 may monitor other blood pressure surrogates such as modulation of cardiogenic components of impedance (e.g., from large field dynamic impedance).

Optionally, multiple RE sensors 102 could be integrated in a nightshirt that includes flexible bands 124 measuring thorax and abdominal efforts. The external device 104 uses the RE signals for differentiating between obstructive and central sleep apnea. The external device 104 also adjusts the treatment in heart failure patients who generally have both types of apneas. Specifically, obstructive sleep apnea may be indicated when the patient exhibits respiratory effort but no inspiration, while central sleep apnea may be indicated when the patient exhibits no inspiration but does not exhibit respiratory effort.

Instead of, or in addition to, the wireless PABP sensor 102, optical sensor(s) 102 may be used to measure oxygen saturation or carbon dioxide saturation. When O2 saturation decreases or CO2 saturation increases beyond a predetermined threshold, alone or in addition to changes in PABP, the system 100 identifies a possible apneic event. The system 100 provides wireless excitation of the receiver/stimulator devices 110/112 to stimulate the phrenic or hypoglossal nerve and intervene in the apneic event. The optical sensor 102 may advantageously be embodied as a lightweight glove or finger cover with red and/or infrared LEDs, such that it is unlikely to inadvertently fall off during the night even during restless sleep, yet still remain comfortable and unobtrusive for the patient and sleeping partner.

Optionally, a galvanic sensor 102 may be used to measure the galvanic skin response, which is an indicator of sympathetic activity. Galvanic or sympathetic skin response is modulated by change in the resting state of the skin and is altered by abnormal physiological changes induced by sleep apneic symptoms. A galvanic sensor 102 will be embedded in a glove or sock to measure the galvanic response from the palms and soles of the patient. These areas are densely innervated by eccrine glands which provides an accurate measure of the galvanic response.

Optionally, the galvanic sensor 102 may be used in a closed-loop system, where galvanic skin data from a patient population with different types of sleep apnea will be collected to implement a galvanic template signature that is unique to the group. The external device 104 uses pattern matching algorithms to compare newly measured and template or baseline signatures to assist in the detection of an apneic event. The neurostimulator devices 110, 112 can be enabled based on a feedback signal from the comparison to prevent an apneic event.

Optionally, the sensors 102 may further comprise a galvanic sensor configured to be positioned against the patient's skin, such as in the patient's hand, chest, foot and the like. The galvanic sensor senses a physiologic state and produces a respiratory effort signal representative of the amount of effort exerted by the patient during respiration.

The system 100 measures the surrogates of respiration during sleep and stimulates muscle(s) or nerve(s) when needed to resume patient breathing. The implantable sensors 102 and stimulation devices 110, 112 of the system 100 may not need batteries, but rather may be comprised of passive components that receive power from a power delivery module such as a mat having RF antenna 106, 108 placed at the patient's bed.

The mattress-top antenna 106, 108 may be configured to broadcast in at least 2 frequency bands. A first frequency is utilized to provide communication and energy transfer to an implanted wireless PABP sensor 112 in the chest, for example a CardioMEMS or similar device. In this way, PABP or other blood pressure may be monitored on a continuous basis, spot-checked at pre-determined intervals, or queried on demand. The on-demand mode may be enabled by including in, or attached to, the antenna 106 a weight sensor 120 or flexible electronics that detect movement related to inhalation and exhalation. The weight sensor 120 detects periodic and non-periodic respiration. When the sensor 120 detects respiration as shifting from periodic to aperiodic, or detects respiration to stop for a period of time (e.g., at least 3 seconds), a measurement of pressure may be triggered.

A second frequency is utilized to provide energy transfer and communication/control signals for the implanted receiver/neurostimulator device(s) 110, 112, such as at the phrenic nerve/diaphragm location. In accordance with embodiments herein, the stimulator devices 110, 112 are passive circuits, with no on-board power source. The passive circuits comprise a receiver antenna tuned to the second frequency and the harmonics of the second frequency, or tuned solely to the second frequency. As used herein, the term "passive circuits", when used in connection with circuitry shall mean that no storage-type power source is provided within or physically connected to the passive circuits. In accordance with embodiments described herein, both a wireless sensor and a wireless stimulator are passive circuits. The wireless sensor and wireless stimulator are provided, without the need for an implantable pulse generator with battery and control circuit implanted. Instead of an implanted pulse generator (with battery and control circuit), embodiments herein are provided such that the heavy processing operations occur at one or more microprocessors that are located outside of the patient's body. Antennas at each of the two frequencies power the wireless sensor and wireless stimulator respectively. Optionally, at least a third frequency that may be used to send control/communication signals, for example instruct the devices 110, 112 to select among a number of stimulation modes or parameters.

The external device 104 may be implemented in various manners such as a bedside monitor or as otherwise described hereafter in connection with various embodiments. The external device 104 includes inputs (e.g., coupled to the antennae 106 and 108) for receiving the IN and RE signals. The external device 104 includes an analysis circuit module 114 and a therapy circuit module 116. The analysis circuit module 114 is configured to analyze the IN signals relative to an IN baseline (e.g., templates, reference IN signals, thresholds) that correspond to normal respiratory behavior. The analysis circuit module 114 performs the comparison with the baseline in order to derive or identify an IN indicator which is representative of differences and/or similarities (and/or a degree of relation) between the IN signals and the IN baseline. Based on the comparison of the IN and IN baselines, the analysis circuit module 114 outputs one or more inspiration indicators.

Optionally, the analysis circuit module 114 may be configured to receive, as the IN signal, a pulmonary artery blood pressure signal that changes over respiratory cycles and represents a surrogate signal for inspiration. The analysis circuit module 114 may declare CSA or OSA states/episodes based on various characteristics of interest from the PABP signal. For example, characteristics of interest in PABP signal may represent a peak to peak (PtP) magnitude of the PABP signal as well as, or alternatively, a period of the PABP signal representing an inspiration cycle. The analysis circuit module 114 declares a CSA or OSA state when the inspiration signal fails to satisfy predetermined criteria, such as a minimum acceptable inspiration peak to peak magnitude. Optionally, the inspiration signal may indicate a CSA or OSA state when the inspiration signal exhibits a period for one respiratory cycle, or one inspiration phase, that exceeds a normally acceptable inspiration period by a predetermined amount (e.g., 130% of a normal inspiration period, and the like).

The analysis circuit module 114 is further configured to analyze the RE signal relative to an RE baseline (e.g. template, reference RE signal or thresholds) that corresponds to a normal amount or degree of respiratory effort exerted by the patient. The measured and RE baselines are compared to derive or identify an RE indicator representative of an amount of difference or degree of variation between the measured and RE baselines. Once the IN and RE indicators are determined, they are stored in memory of the external device 104 and may be transmitted over a network to workstations, physician devices, portable devices, a database and the like.

The IN signals associated with a select sleep event may occur, in time, simultaneous with, prior to, or lagging behind, a corresponding RE signal associated with the same select sleep event. For example, the RE signal may lag in seconds or cycles (e.g. 10-20 seconds, 5-30 cardiac cycles, or 1-5 respiratory cycles) behind a corresponding IN signal. The RE signal may lag behind or precede the IN signal by various amounts of time, numbers of cardiac cycles, or numbers or portions of respiratory cycle(s). The analysis circuit module 114 saves the IN and RE indicators in a temporally correlated manner such that IN and RE indicators are paired as related to a common sleep event. For example, IN and RE indicators may be saved in pairs.

Optionally, the analysis circuit module 114 may add time stamps or other temporal designation to the IN and RE signals/indicators, in order to temporally correlate the IN and RE signals/indicators. For example, segments of the IN signal or indicator for select portions or phases of respiratory cycles may be associated with segments of the RE signal or indicator based on timing information. For example, the analysis circuit module 114 may analyze an IN signal having a select time stamp segment for a first full respiratory cycle (over time $T_1$) or the inspiration phase (over time $P_2$) of a second respiratory cycle to obtain an IN indicator.

The analysis circuit module 114 would obtain the RE indicator by also analyzing an RE signal segment (having a select time stamp) for the same first full respiratory cycle over time $T_1$, or the same inspiration phase $P_2$ of the second respirator cycle.

Optionally, for any given potential apnea event, a segment of the RE signal that is analyzed may be temporally offset from a corresponding segment of the IN signal. For example, an increase in respiratory effort may lag, in time, behind a decrease in inspiration/expiration (e.g., by 2-5 respiration cycles). Hence, when the IN signal is identified to exhibit a potential apnea event at time $T_1$, the system 100 analyze RE signals measured at times $T_2$, $T_3$, or later for an indication of an increase in respiratory effort.

Optionally, the sensor 102 and/or an implanted device may add time stamps or other temporal designation to the IN and RE signals. Alternatively, time stamps may be omitted entirely. Instead, the sensors 102 and/or external device 104 may process the IN and RE signals in real time in a time synchronized manner that avoids any need for time stamps or other temporal designation.

The therapy circuit module 116 is configured to declare a central sleep apnea (CSA) state or an obstructive sleep apnea (OSA) state based on the paired or associated IN and RE indicators. The therapy circuit module 116 also identifies the therapy to be delivered, such as an OSA or CSA therapy, based upon the OSA or CSA state that is declared. Optionally, the therapy circuit module 116 may target, with the CSA therapy, nerve stimulation at a phrenic nerve when a CSA state is declared to exist. Optionally, the therapy circuit module 116 may target muscle stimulation at the diaphragm when a CSA state is declared. Alternatively or in addition, the therapy circuit module 116 may identify a therapy that is configured to target nerve stimulation at the hypoglossal nerve and/or muscle stimulation at the oropharyngeal muscles when the OSA state is declared. As explained herein, therapies may be adjusted (intensified) during successive iterations through delivery of treatments when a particular therapy is not successful.

For patients suffering from obstructive sleep apnea, a receiver/stimulator device 110 may be implanted near the hypoglossal nerve. To communicate with the receiver/stimulator device 110, either the mattress-top antenna 106 may be configured with a form factor large enough to communicate with both the pressure sensor 102 implanted in the chest and the stimulator device 110 in the head/neck, or a second antenna 108 may be provided within or near the patient's pillow and configured to communicate with the receiver/stimulator device 110.

The antennas 106, 108 are made from flexible materials and of slim form factor. The antenna 106, 108 may be placed between the patient's mattress and bedsheets or within the pillowcase, in order to be in close proximity to the implanted sensors 102 and stimulator devices 110, 112 without interfering with the comfort of the bed. The antennas 106, 108 are connected to an external device 104 that provides the power for communication, analyzes the sensor data and determines when nerve or muscle stimulation is required to intervene in an apneic event. The external device 104 may optionally and advantageously be connected to the internet for providing trending and diagnostics to a clinician and reports back to the patient.

Optionally, a quad-frequency-band version of the system 100 may be employed for use among households where both sleeping partners have a form of sleep apnea. For example, first and second frequency are used to communicate with the sensor 102 and receiver/stimulator devices 110, 112 respectively for the first partner, and a third and fourth frequency are used to communicate with the sensor 102 and receiver/stimulator devices 110, 112 respectively for the second partner.

Optionally, a 3-D accelerometer or other position sensor 122 may be incorporated with the pressure sensor 102. Alternatively, weight and position sensors 120 may be incorporated into the antenna 106 on the mattress. The sensors 120, 122 collect data regarding the patient's position over one or multiple sleep cycles and use the data. For example, the data is used for diagnostics & trending, wherein histograms of number and duration of apneic events are created according to sleep position. The trends can be used to help train the patient to sleep in different positions that are less prone to apnea events. The data may be used for prediction of apneic events, such as when patients are detected to be in positions more strongly associated with apnea. Optionally, the neurostimulation device 110, 112 may be enabled proactively in order avoid a likely impending apneic event. The data may be used for modulation of detection thresholds. For example, different patient positions may cause variations in PABP or other surrogates for apnea. Different patient positions may cause the sensors 110, 112 to have different sensitivity and thus correlation with true apneic events. Thus, a different threshold may be used before triggering anti-apneic stimulation, based at least in part on the patient's present sleep posture.

Today, many patients already having implantable cardiac devices. Optionally, existing IMDs may be reconfigured for detecting respiration surrogates, blood pressure surrogates, blood gas saturation surrogates, etc. Once reconfigured, the system 100 may communicate with implantable cardiac devices and read such diagnostic data for use as a replacement for, or in addition to, the other apnea detection sensors 102 described herein.

Figure 1B:
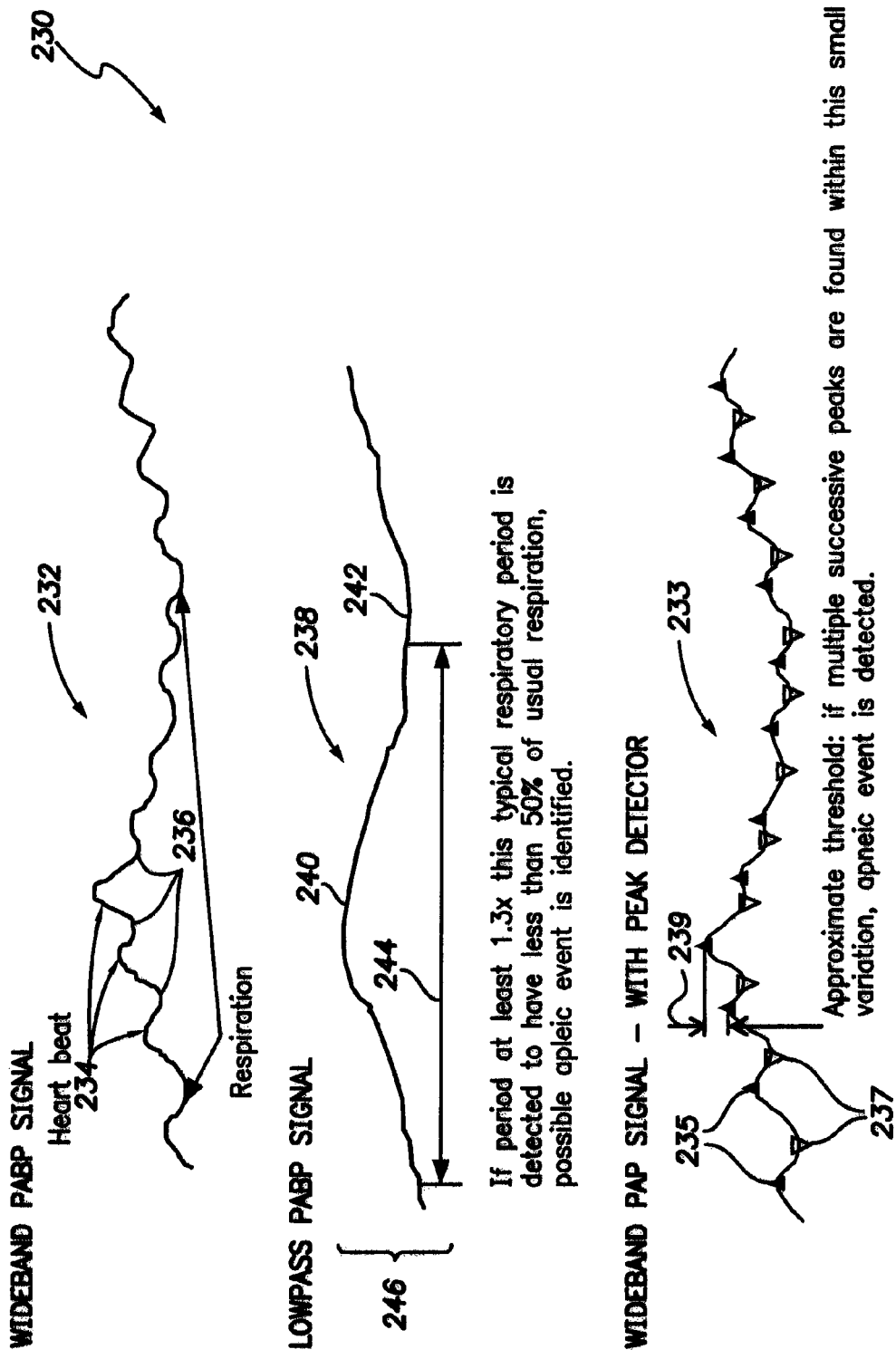
FIG. 1B illustrates blood pressure graphs with multiple signals plotted over time (along the horizontal axis) formed in accordance with an embodiment.

FIG. 1B illustrates a blood pressure (BP) graph 230 with multiple signals plotted over time (along the horizontal axis). A BP signal 232 represents a wide frequency band pulmonary blood pressure signal that is sensed by a blood pressure sensor 102 in accordance with an embodiment. The BP graph 230 plots pulmonary blood pressure along the vertical axis. The BP signal 232 includes multiple local maximum and minimum cardiac-related peaks 234 and 236 that represent the pulmonary blood pressure at certain points in the cardiac cycle. For example, the peaks 234 represent end systole point in the cardiac cycle, while the valleys 236 represent the end diastole point in the cardiac cycle.

In accordance with embodiments herein, the BP signal 232 is low pass filtered to form a lowpass PABP signal 238 which has fewer peaks and valleys as compared to the BP signal 232. The lowpass PABP signal 238 includes maximum and minimum respiratory-related peaks 240 and 242 during each respiratory period 244. A peak to peak (PtP) magnitude 246 between the maximum and minimum respiratory-related peaks 240 and 242 is representative of a degree, depth or strength of the patient inspiration and/or expiration. For example, the magnitude 246 may increase for a current breathing cycle relative to a prior or baseline magnitude 246 when the patient exhibits a deeper or stronger inspiration/expiration as compared to a baseline inspiration/expiration (e.g., when the patient is dreaming). For example, the magnitude 246 may decrease for a current breathing cycle relative to a prior or baseline magnitude 246 when the patient exhibits a shallow or weaker inspiration/expiration as compared to a baseline inspiration/expiration (e.g., when the patient is experiencing deep sleep or an apnea event).

The respiratory period 244 corresponds to the period of time over which a patient completes an inspiration and expiration cycle. For example, the period 244 may decrease for a current breathing cycle relative to a prior or baseline period when the patient exhibits quicker inspiration/expiration phases as compared to baseline inspiration/expiration phases (e.g., when the patient is dreaming). For example, the period 244 may increase for a current breathing cycle relative to a prior or baseline magnitude 246 when the patient exhibits shallow or slower inspiration/expiration phases as compared to a baseline inspiration/expiration (e.g., when the patient is experiencing deep sleep or an apnea event). The lowpass PABP signal 238 represents an accurate, well-correlated surrogate for inspiration/expiration behavior of the patient without directly measuring inspiration/expiration. Accordingly, in an embodiment, the lowpass PABP signal 238 is utilized as the inspiration signal that is analyzed, relative to an IN baseline (e.g., baseline lowpass PABP signal).

Optionally, a BP signal 233 may be utilized as the inspiration signal without lowpass filtering. FIG. 1B illustrates a second BP signal 233 that may be sensed by the sensor 102. The BP signal 233 includes multiple local maximum and minimum cardiac-related peaks 235 and 237 that represent the pulmonary blood pressure at certain points in the cardiac cycle. The method and system may utilize a peak detection process/module to identify the peaks 235 and 237, as well as the PtP magnitude 239 between successive positive peaks 235. Optionally, the PtP magnitude 239 may be measured between successive negative peaks 237. A baseline PtP threshold may be defined in connection with an IN baseline, where the baseline PtP threshold represents a minimum acceptable variation or different in magnitude when a patient is experiencing normal inspiration/expiration. However, when the patient is experiencing CSA or OSE, the PtP magnitude between successive peaks 235 decreases such that multiple successive peaks 235 (or multiple peaks 235 occurring within a predetermined limited period of time). When multiple measured PtP magnitudes 239 (successively or within a predetermined limited period of time) are identified to fall within/below the baseline threshold, the patient is considered to be experiencing an OSA or CSA episode.

Apnea Detection Method

Figure 3A:
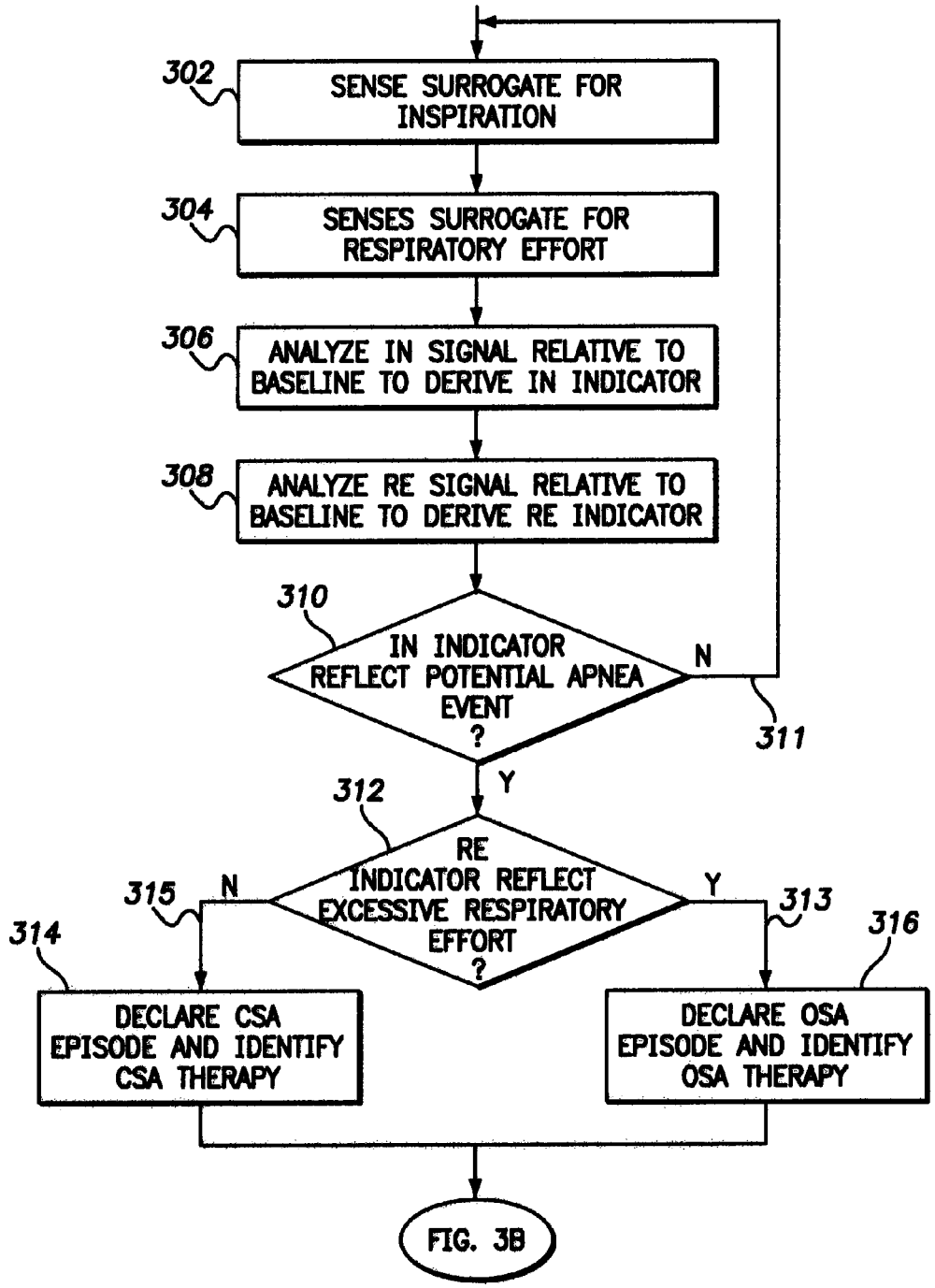
FIG. 3A illustrates a process implemented in accordance with an embodiment for treating sleep apnea using implantable sensors and device.
Figure 3B:
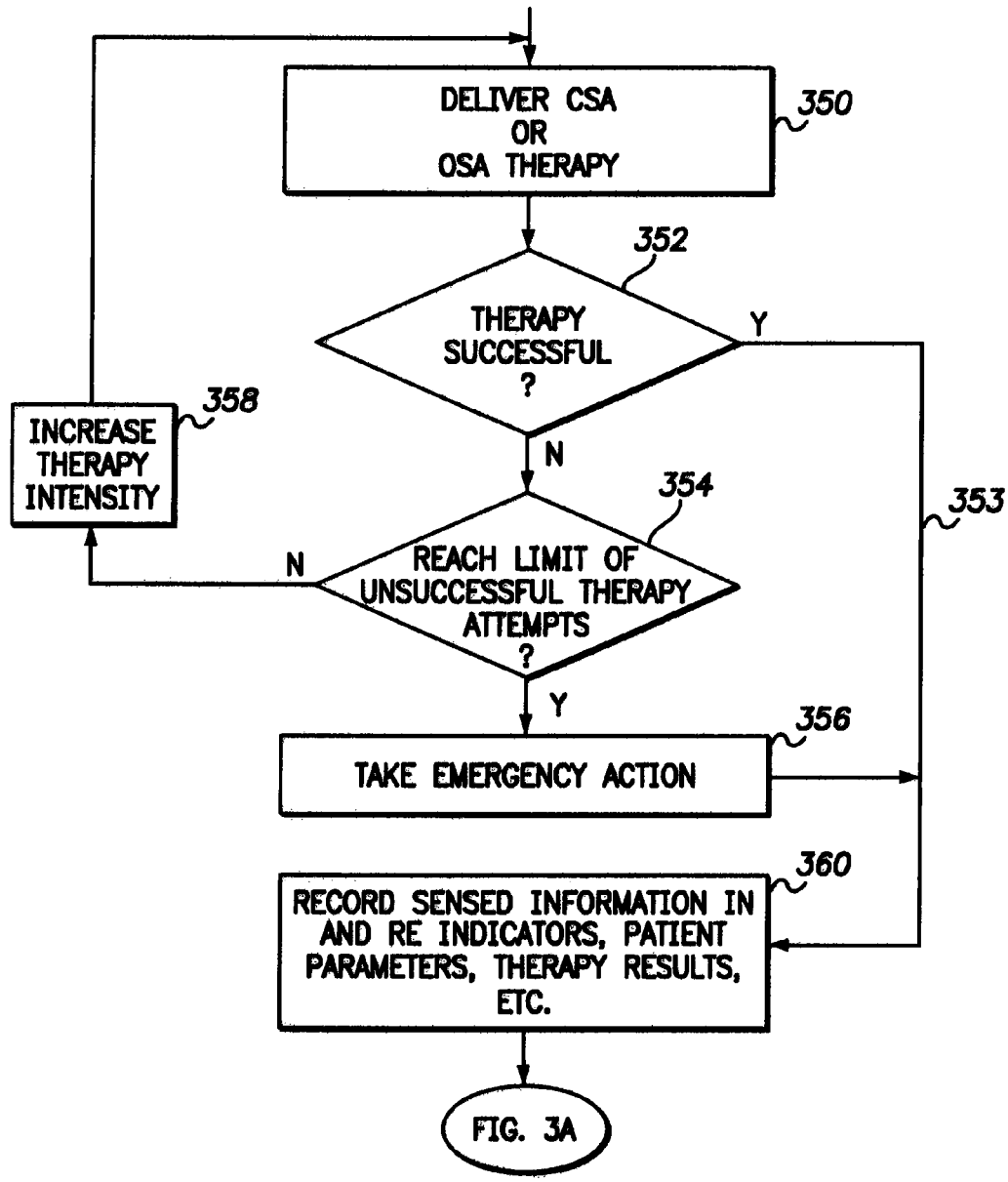
FIG. 3B illustrates a process carried out in accordance with an embodiment for delivering central or obstructive sleep apnea therapy.

FIGS. 3A and 3B illustrate a process implemented in accordance with an embodiment for detecting and treating sleep apnea using implantable and external sensors and devices. At 302, the method senses an inspiration (IN) signal representative of inspiration, experienced by patient as a respiratory surrogate signal. The respiratory surrogate signal may be one of numerous surrogate signals detected by the various structures described herein. Optionally, the sensing operation may include sensing at least one of a blood pressure or a blood oxygen saturation level from a blood pressure sensor or blood oxygen saturation level respectively. Optionally or in addition, the sensing operation may include receiving a pulmonary artery blood pressure (PABP) signal (e.g., pulmonary arterial pressure) that changes over respiratory cycles as the surrogate signal for inspiration. The PABP signal includes an indication of a magnitude and a period of each individual inspiration cycle experienced by the patient. The PABP signal may be low pass filtered with a filter having a cut off frequency at a predetermined frequency level to generate a low pass filtered PABP signal. The PABP low pass filtered signal increases and decreases in magnitude and exhibits a period, in accordance with changes in the patient's inspiration over the respiratory cycle.

At 304, the method senses a respiratory effort signal representative of an amount of effort exerted by the patient during respiration. The manner by which the respiratory effort is measured and the corresponding RE signal generated, are described herein in connection with various embodiments.

At 306, the method analyzes the inspiration signal relative to an IN baseline that corresponds to normal respiratory behavior. The analysis at 306 seeks to identify an IN indicator. The IN baseline may be preprogrammed by a user, measured from the patient while the patient is experiencing normal inspiration, or derived from preexisting patient data from the present patient or from a larger patient population. The IN baseline may be updated periodically throughout operation to account for normal variations in the patient's inspiration behavior. Optionally, new baseline inspiration information may be downloaded to an implantable device or external device, periodically from a remote server over a network as new baseline inspiration information becomes available.

At 308, the method analyzes the respiratory effort signal also based on an RE baseline. The RE baseline corresponds to a normal amount of respiratory effort exerted by the patient. The analysis at 308 seeks to identify an RE indicator. The RE baseline may be preprogrammed by a user, corrected from the present patient when experiencing a normal amount of respiratory effort, generated based on preexisting information about the present patient or a patient's population, and the like. The RE indicator represents a measure of a difference between the sensed RE signal and RE baseline. For example, the RE indicator may represent an amount of variance between the measured and the RE baselines.

Alternatively, the IN and RE indicators may be derived at 306 and 308 from various mathematical calculations that compare and quantify differences between two or more signals, such as through auto correlation, comparisons of a number of peaks exhibited in each measured and baseline signal, the period of the signals, the peak to peak amplitudes of the signals, differences in the areas under the curves, and the like.

At 310, the method analyzes the IN indicator to determine whether the IN indicator reflects a potential apnea event. For example, the method may compare the IN indicator to a threshold that is predetermined or automatically derived throughout operation. Accordingly, when, at 310, a potential apnea event is identified, flow moves to 312. When the inspiration indicator at 310 is determined to not reflect a potential apnea event, flow moves along path 311 to wait for a predetermined period of time before beginning the next sensing operation. When the inspiration indicator exceeds the threshold, this may be an indication that the patient is experiencing a potential apnea event. Based only on certain types of inspiration signals, the method may not discriminate between whether the patient is experiencing central or obstructive sleep apnea.

At 312, the method analyzes the RE indicator to determine whether the RE indicator reflects the potential that the patient is experiencing excessive respiratory effort. For example, the RE indicator may be compared to a threshold that is predetermined or automatically updated. When the RE indicator exceeds the threshold, this may indicate that an excessive amount of respiratory effort is being experienced by the patient. When, at 312, it is determined that the patient is experiencing excessive respiratory effort, flow moves along branch 313 to the operation at 316. Alternatively, flow moves along branch 315 to the operation at 314.

At 316, the method declares the patient to be experiencing an obstructive sleep apnea episode and identifies a corresponding OSA therapy. For example, the method at 316 may access memory within the implantable device or external device to obtain the parameters associated with an OSA therapy. Optionally, multiple OSA therapies may be available, in which case the method selects at 316 from one of the multiple OSA therapies. The selection of one of the multiple OSA therapies may be based upon the signature of the IN and/or RE signals, and/or alternatively upon prior histories of the patient. For example, if a patient experiences multiple OSA episodes in a short period of time, the method may select a more aggressive OSA therapy. Optionally, when the level or degree of respiratory effort is determined to be increasing relative to prior OSA episodes (e.g., over the course of an evening), the method at 316 may also select a more aggressive OSA therapy. Various OSA therapies may differ in terms of the amplitude of stimulation, number of pulses delivered during a single stimulation episode, location(s) at which the stimulation is/are delivered and the like.

Optionally, the OSA therapy may be configured to target nerve stimulation at the hypoglossal nerve when the method declares an OSA episode or state. Optionally, or additionally, the OSA therapy may be configured to target muscle stimulation at the oropharyngeal muscles when the method declares the OSA episode or state.

Returning to 312, when the RE indicator denotes that the patient is not experiencing excessive respiratory effort, flow moves along 315 to the operation at 314.

At 314, the method declares the patient to be experiencing a central sleep apnea episode and identifies a corresponding CSA therapy to be delivered. As explained above in connection with OSA therapies, the implantable device and/or external device may save a single CSA therapy that is delivered each time flow moves to 314. Optionally, the implantable device or external device may store multiple CSA therapies having different levels of aggressiveness. For example, the method of 314 may select a less aggressive CSA therapy the first time a patient experiences a CSA episode in one evening, with progressively stronger or more aggressive therapies (e.g. stronger stimulus, longer pulses, more pulses, etc.) delivered over the course of the evening during subsequent CSA episodes. Alternatively, the CSA therapy may be varied based upon the nature or the signature of the RE and IN signals which may indicate different types or levels of CSA episodes. For example, when an inspiration signal indicates, based on the waveform or signature of the inspiration signal, that a patient is experiencing a potentially dangerous CSA episode, at 314 a more aggressive CSA therapy may be selected.

Optionally, the CSA therapy may include delivering at least one of a nerve stimulation or a muscle stimulation configured to induce breathing. For example, the CSA therapy may include stimulations that are targeted for nerve stimulation at the phrenic nerve when the method declares the CSA state or episode to exist. Optionally, the CSA therapy may be configured to target muscle stimulation at a diaphragm of the patient when the CSA episode or state is declared.

Once the CSA and/or OSA therapies are identified at 314 and 316, flow moves to FIG. 3B where a therapy is delivered.

FIG. 3B illustrates a process carried out in accordance with an embodiment for delivering central or obstructive sleep apnea therapy. At 350, the CSA or OSA therapy is delivered. The therapy may be delivered upon detection of a change or secession of a respiratory related blood pressure oscillations sensed from a sensor in the pulmonary artery. Alternatively or in addition, the therapy may be delivered upon detection of reduced oxygen saturation in a sensor in the pulmonary arterial blood flow or superior vena cava.

At 352, the method measures additional patient parameters, such as new inspiration signals and/or new respiratory effort signals, to determine whether the therapy was successful. When the therapy is successful, flow moves along branch 353. Alternatively, when the therapy is not successful, flow moves to 354.

At 354, the method determines whether a series of therapies have already been delivered (e.g., two to ten therapy sessions over a one to two minute period of time). The number of unsuccessful therapy attempts may be varied, based on the nature of the sleep apnea. For example, when substantial obstructive sleep apnea is occurring, fewer unsuccessful therapies may be permitted at 354. Alternatively, when the IN and/or RE signals indicate that the nature or signature of the CSA or OSA episode is not unduly dangerous, the method at 354 may permit more therapy attempts to be performed. When at 354, the method determines that a limit of unsuccessful therapy attempts has been reached, flow moves to 356.

At 356, a predetermined emergency action is taken, such as delivering another type of stimulus sufficient to wake up the patient. Alternatively, the emergency action may be to trigger an alarm on the bedside external device. Alternatively or in addition, at 356, the emergency action may be to nullify a physician or directly contact emergency services personnel such as a hospital or ambulance.

Returning to 354, when the method determines that the number of therapies that have been attempted is less than a limit, flow moves to 358. At 358, the method increases the intensity of the therapy. For example, the therapy intensity may be increased by increasing the amplitude of the stimulus, the duration of the stimulus, the number of stimulus pulses, the locations at which stimulus are applied and the like. Once the therapy intensity is increased, the flow returns to 350, where the updated/new therapy is delivered. Next, the operations at 352 and 354 are repeated.

When the therapy is successful at 352, flow moves along 353 to the function at 360. At 360, the implantable device and/or external device record various information regarding the sleep apnea episode. For example the IN and RE signals that were sensed may be recorded for a desired period of time preceding and following the apnea event. The IN and RE indicators may be recorded, as well as other patient parameters of interest, such as heart rate, blood pressure, patient's position, patient's movement and the like. In addition, therapy results may be recorded as well as other information of interest in the memory of the external device and/or implantable device. Once the operations at 360 are performed, both following successful termination of an apnea event as well as following an emergency action (at 356) flow returns to FIG. 3A where new inspiration and respiratory effort surrogate signals are sensed.

Implantable Neurostimulation Device

Figure 2A:
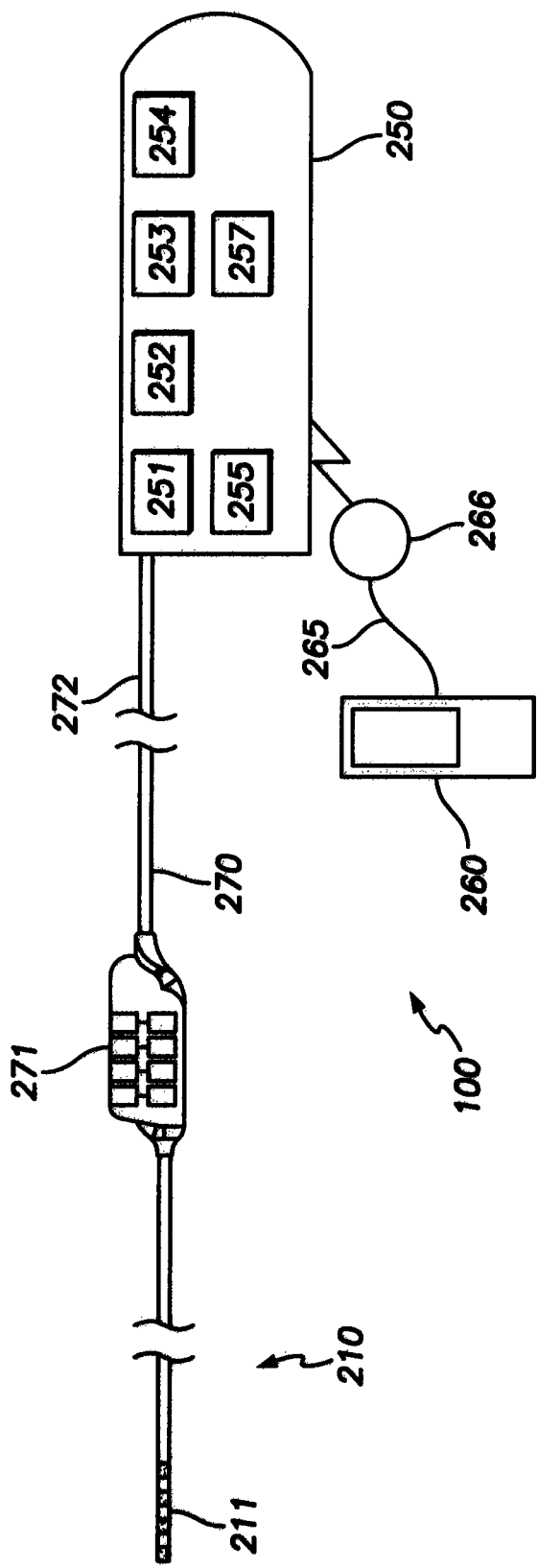
FIG. 2A depicts a stimulation system that may be used to generate electrical pulses for application to tissue of a patient according to one embodiment.

FIG. 2A depicts a stimulation system 200 that may be used to generate electrical pulses for application to tissue of a patient according to one embodiment. For example, system 200 may be adapted to stimulate spinal cord tissue, peripheral nerve tissue, the phrenic nerve, the hypoglossal nerve, the diaphragm, the oropharyngeal muscle, deep brain tissue, cortical tissue, cardiac tissue, digestive tissue, pelvic floor tissue, or any other suitable tissue within a patient's body. The system includes a pulse generator 250, a lead 210 and a controller device 260. The pulse generator 250 and lead 210 represent one embodiment to implement the stimulator devices 110, 112. The controller device 260 represents one embodiment for the external device 104. Optionally, the lead 210 may also perform sensing of IN and/or RE signals.

In accordance with embodiments herein, the pulse generator 250 and lead 210 are passive circuits. In one embodiment, the pulse generator 250 is physically connected to the lead 210. Optionally, the pulse generator 250 and lead 210 are not physically connected to one another. The pulse generator 250 and lead 210 receive power through one or more wireless links. The lead 210 and/or pulse generator 250 wirelessly receive signals and power from a remote microprocessor and perform stimulation based on signals received-over a wireless link.

Certain components such as the lead 210 and/or pulse generators 250 are implanted and comprise an implanted antenna and very basic passive circuitry capable of converting signals received from the antenna into power and stimulation at a predetermined or programmed frequency and amplitude. The remainder of the system including a communication antenna and the majority of the controller, power supply, etc., reside outside the body preferably in a bedside unit. Similarly, the sensing component is a wireless implantable blood pressure sensor with an antenna and minimal passive circuitry to convert signals received by the antenna from an external unit into sufficient power and control signals to transiently power the blood pressure sensor and relay the signal back to the external antenna, while the external components provide the power for the implanted sensor, perform the analysis, and communicate with the therapy module as needed.

The implantable pulse generator 250 (e.g., devices 110, 112 in FIG. 1A) is adapted to generate electrical pulses for application to tissue of a patient. Implantable pulse generator 250 typically comprises a metallic housing that encloses controller 251, pulse generating circuitry 252, temporary chargeable components (e.g., capacitors) 253, far-field and/or near-field communication circuitry 255, switching circuitry 257, etc. of the device. Controller 251 typically includes a microcontroller or other suitable processor for controlling the various other components of the device. Software code is typically stored in memory of the pulse generator 250 for execution by the microcontroller or processor to control the various components of the device.

Pulse generator 250 may comprise a separate or an attached extension component 270. If extension component 270 is a separate component, extension component 270 may connect with the "header" portion of pulse generator 250 as is known in the art. If extension component 270 is integrated with pulse generator 250, internal electrical connections may be made through respective conductive components. Within pulse generator 250, electrical pulses are generated by pulse generating circuitry 252 and are provided to switching circuitry 257. The switching circuit connects to outputs of pulse generator 250. Electrical connectors (e.g., "Bal-Seal" connectors) within connector portion 271 of extension component 270 or within the IPG header may be employed to conduct the stimulation pulses. The terminals of one or more stimulation leads 210 are inserted within connector portion 271 or within the IPG header for electrical connection with respective connectors. Thereby, the pulses originating from pulse generator 250 are provided to stimulation lead 210. The pulses are then conducted through the conductors of lead 210 and applied to tissue of a patient via electrodes 221. Any suitable known or later developed design may be employed for connector portion 271.

For implementation of the components within pulse generator 250, a processor and associated charge control circuitry for an implantable pulse generator is described in U.S. Patent Publication No. 20060259098, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Ser. No. 11/109,114, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 20060170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within pulse generator 250. Different pulses on different electrodes may be generated using a single set of pulse generating circuitry using consecutively generated pulses according to a "multi-stimset program" as is known in the art. Complex pulse parameters may be employed such as those described in U.S. Pat. No. 7,228,179, entitled "Method and apparatus for providing complex tissue stimulation patterns," and International Patent Publication Number WO/2001/093953 A1, entitled "NEUROMODULATION THERAPY SYSTEM," which are incorporated herein by reference. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 210 may comprise a lead body of insulative material about a plurality of conductors within the material that extend from a proximal end of lead 210 to its distal end. The conductors electrically couple a plurality of electrodes 221 to a plurality of terminals (not shown) of lead 210. The terminals are adapted to receive electrical pulses and the electrodes 221 are adapted to apply stimulation pulses to tissue of the patient. Also, sensing of physiological signals may occur through electrodes 221, the conductors, and the terminals. Additionally or alternatively, various sensors (not shown) may be located near the distal end of stimulation lead 210 and electrically coupled to terminals through conductors within the lead body 272. Stimulation lead 210 may include any suitable number of electrodes 221, terminals, and internal conductors.

Figure 2D:
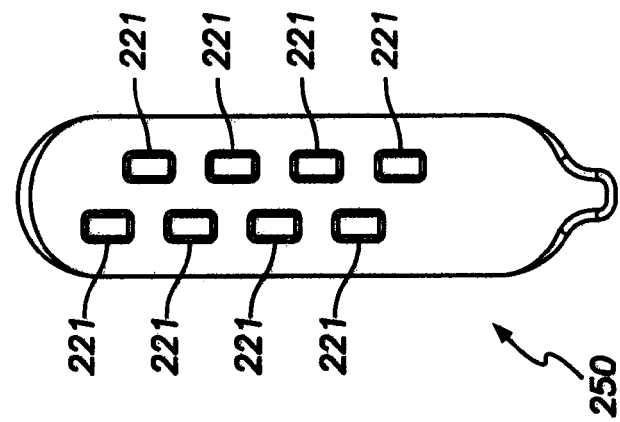
FIG. 2D depicts a sensing stimulation portion for inclusion at the distal end of a lead formed in accordance with an embodiment.
Figure 2C:
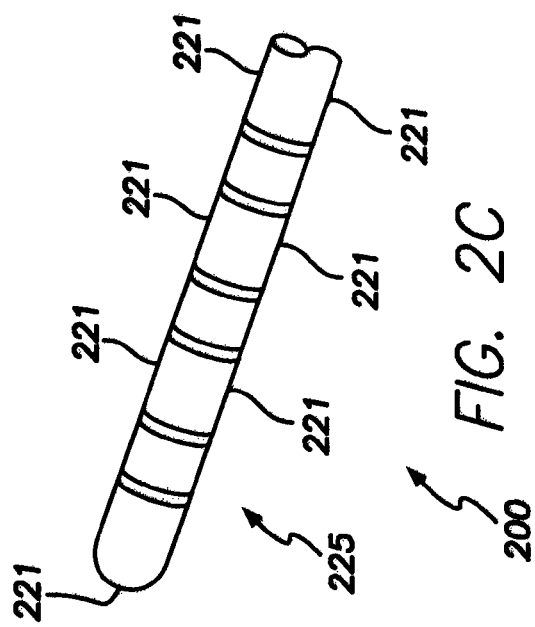
FIG. 2C depicts a sensing and/or stimulation portion for inclusion at the distal end of a lead formed in accordance with an embodiment.
Figure 2B:
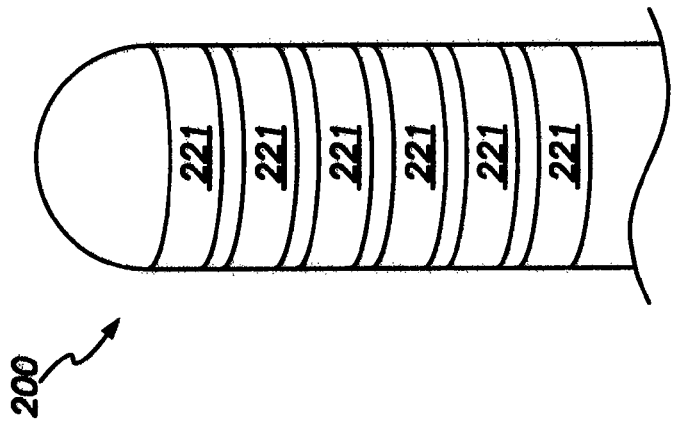
FIG. 2B depicts a sensing stimulation portion for inclusion at the distal end of a lead formed in accordance with an embodiment.

FIGS. 2B-2D respectively depict sensing stimulation portions 200, 225, and 250 for inclusion at the distal end of lead 210. Stimulation portion 200 depicts a conventional stimulation portion of a "percutaneous" lead with multiple ring electrodes. Sensing and/or stimulation portion 225 depicts a stimulation portion including several "segmented electrodes." The term "segmented electrode" is distinguishable from the term "ring electrode." As used herein, the term "segmented electrode" refers to an electrode of a group of electrodes that are positioned at the same longitudinal location along the longitudinal axis of a lead and that are angularly positioned about the longitudinal axis so they do not overlap and are electrically isolated from one another. Example fabrication processes are disclosed in U.S. patent application Ser. No. 12/895,096, entitled, "METHOD OF FABRICATING STIMULATION LEAD FOR APPLYING ELECTRICAL STIMULATION TO TISSUE OF A PATIENT," which is incorporated herein by reference. Stimulation portion 250 includes multiple planar electrodes on a paddle structure.

Although not required for all embodiments, the lead bodies of lead(s) 210 and extension component 270 may be fabricated to flex and elongate in response to patient movements upon implantation within the patient. By fabricating lead bodies according to some embodiments, a lead body or a portion thereof is capable of elastic elongation under relatively low stretching forces. Also, after removal of the stretching force, the lead body is capable of resuming its original length and profile. For example, the lead body may stretch 10%, 20%, 25%, 35%, or even up or above to 50% at forces of about 0.5, 1.0, and/or 2.0 pounds of stretching force.

The ability to elongate at relatively low forces may present one or more advantages for implantation in a patient. For example, as a patient changes posture (e.g., "bends" the patient's back), the distance from the implanted pulse generator to the stimulation target location changes. The lead body may elongate in response to such changes in posture without damaging the conductors of the lead body or disconnecting from pulse generator. Also, deep brain stimulation implants, cortical stimulation implants, and occipital subcutaneous stimulation implants usually involve tunneling of the lead body through tissue of the patient's neck to a location below the clavicle. Movement of the patient's neck subjects a stimulation lead to significant flexing and twisting which may damage the conductors of the lead body. Due to the ability to elastically elongate responsive to movement of the patient's neck, certain lead bodies according to some embodiments are better adapted for such implants than some other known lead body designs. Fabrication techniques and material characteristics for "body compliant" leads are disclosed in greater detail in U.S. Provisional Patent Application Ser. No. 60/788,518, entitled "Lead Body Manufacturing," filed Mar. 31, 2006, which is incorporated herein by reference.

A "wand" 265 may be electrically connected to controller device through suitable electrical connectors (not shown). The electrical connectors are electrically connected to coil 266 (the "primary" coil) at the distal end of wand 265 through respective wires (not shown). Typically, coil 266 is connected to the wires through capacitors (not shown). Also, in some embodiments, wand 265 may comprise one or more temperature sensors for use during charging operations.

The patient then places the primary coil 266 against the patient's body immediately above the secondary coil (not shown), i.e., the coil of the implantable medical device. Preferably, the primary coil 266 and the secondary coil are aligned in a coaxial manner by the patient for efficiency of the coupling between the primary and secondary coils. Controller 260 generates an AC-signal to drive current through coil 266 of wand 265. Assuming that primary coil 266 and secondary coil are suitably positioned relative to each other, the secondary coil is disposed within the field generated by the current driven through primary coil 266. Current is then induced in secondary coil. The current induced in the coil of the implantable pulse generator is rectified and regulated by charging circuitry 254 to deliver charge to the temporary chargeable component 253. Charging circuitry 254 may also communicate status messages to controller 260 during charging operations using pulse-loading or any other suitable technique. For example, controller 260 may communicate the coupling status, charging status, charge completion status, etc.

External controller device 260 (e.g., external device 104 in FIG. 1A) is also a device that permits the operations of pulse generator 250 to be controlled by the user after pulse generator 250 is implanted within a patient, although in alternative embodiments separate devices are employed for charging and programming. Also, multiple controller devices may be provided for different types of users (e.g., the patient or a clinician). Controller device 260 can be implemented by utilizing a suitable handheld processor-based system that possesses wireless communication capabilities. Software is typically stored in memory of controller device 260 to control the various operations of controller device 260. Also, the wireless communication functionality of controller device 260 can be integrated within the handheld device package or provided as a separate attachable device. The interface functionality of controller device 260 is implemented using suitable software code for interacting with the user and using the wireless communication capabilities to conduct communications with IPG 250.

Controller device 260 preferably provides one or more user interfaces to allow the user to operate pulse generator 250. The user interfaces may permit the user to move electrical stimulation along and/or across one or more stimulation leads using different electrode combinations, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is incorporated herein by reference. Also, controller device 260 may permit operation of IPG 250 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. IPG 250 modifies its internal parameters in response to the control signals from controller device 260 to vary the stimulation characteristics of stimulation pulses transmitted through stimulation lead 210 to the tissue of the patient. Neurostimulation systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference.

Implantable Medical Device

Figure 4:
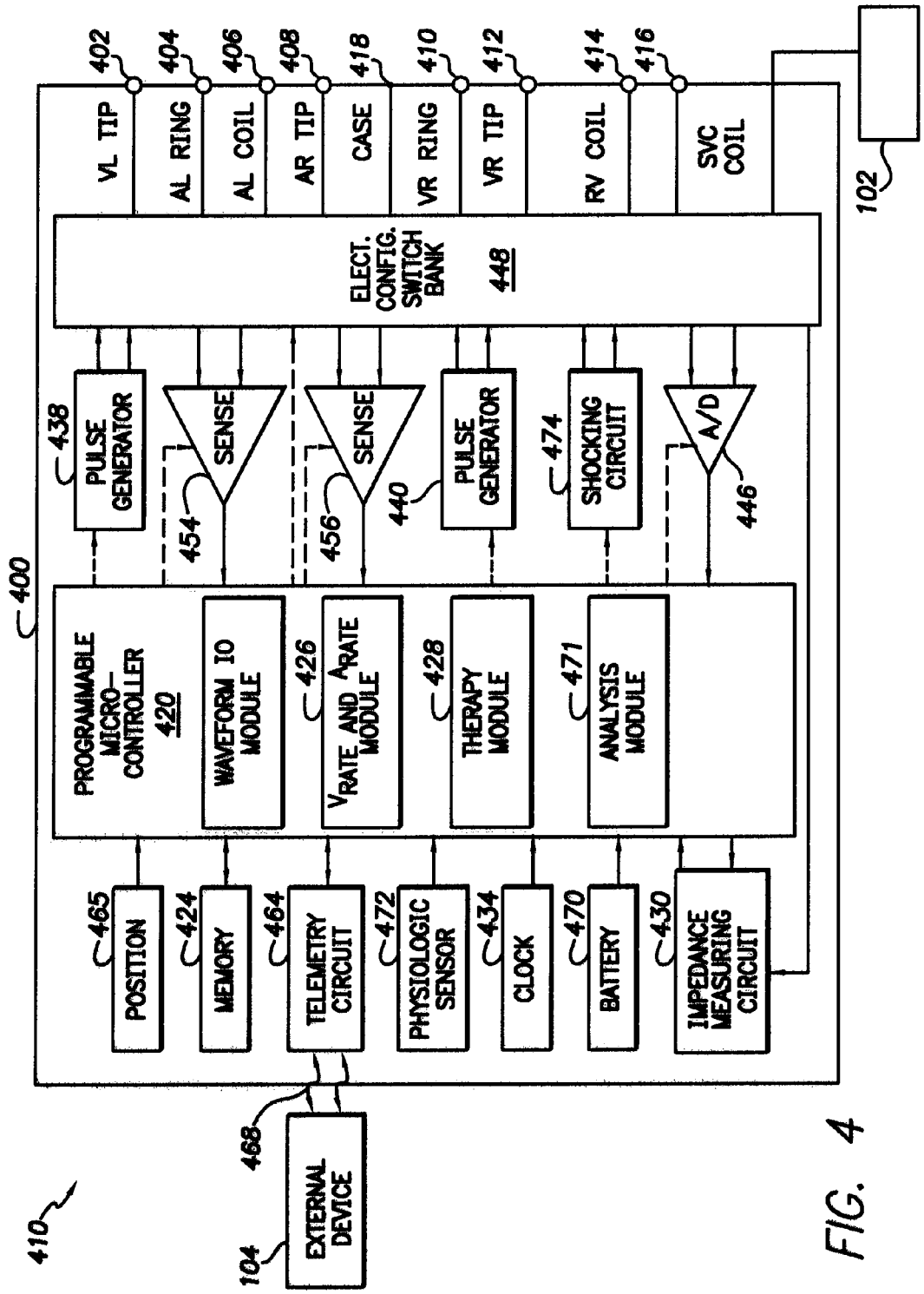
FIG. 4 illustrates a block diagram of exemplary internal components of an implantable medical device formed in accordance with an embodiment.

FIG. 4 illustrates a block diagram of exemplary internal components of the IMD 410. The IMD 410 may be configured to perform all or a portion of the operations described in connection with FIGS. 3A and 3B, in addition to pacemaker and/or defibrillator operations. The systems described herein can include or represent hardware and associated instructions (e.g., software stored on a tangible and non-transitory computer readable storage medium, such as a computer hard drive, ROM, RAM, or the like) that perform the operations described herein. The hardware may include electronic circuits that include and/or are connected to one or more logic-based devices, such as microprocessors, processors, controllers, or the like. These devices may be off-the-shelf devices that perform the operations described herein from the instructions described above. Additionally or alternatively, one or more of these devices may be hard-wired with logic circuits to perform these operations.

The IMD 410 is for illustration purposes only, and it is understood that the circuitry could be duplicated, eliminated or disabled in any desired combination to provide a device capable of treating the appropriate nerves, muscle and/or heart chamber(s) with cardioversion, defibrillation and/or pacing stimulation as well as providing for apnea detection and therapy. The housing 400 for the IMD 410, shown schematically in FIG. 4, is often referred to as the "can", "case" or "case electrode" and may be programmably selected to act as the return electrode for all "unipolar" modes. The housing may further be used as a return electrode alone or in combination with one or more of the coil electrodes for shocking purposes. The housing further includes a connector (not shown) having a plurality of terminals, 402 to 416. The terminals 402-416 may be connected to various types of electrodes located proximate to nerve, muscle or cardiac tissue in order to deliver stimulus to nerves, muscles and/or cardiac tissue.

The IMD 410 includes a programmable microcontroller 420 which controls operation. The microcontroller 420 (also referred to herein as a processor module or unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 420 includes the ability to process or monitor input signals (data) as controlled by program code stored in memory. The details of the design and operation of the microcontroller 420 are not critical to the invention. Rather, any suitable microcontroller 420 may be used that carries out the functions described herein. Among other things, the microcontroller 420 receives, processes, and manages storage of digitized data sets from the various sensors and electrodes. For example, the data sets may include IN signals, ER signals, IEGM data, pressure data, heart sound data, and the like.

The IMD 410 includes a nerve pulse generator 438 and a muscle pulse generator 440 to generate stimulation pulses for delivery via an electrode configuration switch 448. The pulse generators, 438 and 440, may include dedicated, independent pulse generators, multiplexed pulse generators or shared pulse generators. The pulse generators, 438 and 440, are controlled by the microcontroller 420 via appropriate control signals, respectively, to trigger or inhibit the stimulation pulses.

The microcontroller 420 further includes timing control circuitry used to control the timing of such stimulation pulses (e.g., OSA therapy, CSA therapy, pacing rate, atria-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, and the like. Switch 448 includes a plurality of switches for connecting the desired electrodes to the appropriate I/O circuits, thereby providing complete electrode programmability including how and where to deliver OSA and CSA therapies. Accordingly, the switch 448, in response to a control signal from the microcontroller 420, determines the polarity of the stimulation pulses (e.g., unipolar, bipolar, etc.) by selectively closing the appropriate combination of switches (not shown) as is known in the art. The switch 448 connects to the sensors 102 to collect IN and RE signals.

Sensing circuits 454 and 456 may also be selectively coupled to various sensors 102, electrodes and/or leads through terminals 402-416 and the switch 448 for detecting IN and RE signals, and/or the presence of select activity (nerve, muscle or cardiac). Accordingly, the sensing circuits, 454 and 456, may include dedicated sense amplifiers, multiplexed amplifiers or shared amplifiers. The outputs of the sensing circuits, 454 and 456, are connected to the microcontroller 420 which, in turn, are able to trigger or inhibit the pulse generators, 438 and 440, respectively.

Pulmonary arterial pressure, blood oxygen saturation, galvanic or other IN or RE signals are also applied to the inputs of an analog-to-digital (A/D) data acquisition system 446. The data acquisition system 446 is configured to acquire IN and/or RE signals, convert the raw analog data into a digital IN and/or RE signal, and store the digital signals in memory 424 for later processing and/or telemetric transmission to an external device 104. The data acquisition system 446 is coupled to various sensors 102 through the switch 448 to sample signals across any combination of desired electrodes. The data acquisition system 446 acquires, performs A/D conversion, produces and saves the digital data.

The controller 420 includes an analysis module 471 that functions in accordance with embodiments described herein. The analysis module 471 analyzes characteristics of interest from the IN and RE signals. The controller 420 may utilize different combinations of the electrodes to deliver different stimulus when analyzing the characteristic of interest. As another example, the controller 420 may utilize different timing configurations when analyzing the characteristic of interest. The analysis module 471 may analyze various signals from a variety of sensors to detect characteristics of interest.

The microcontroller 420 is coupled to memory 424 by a suitable data/address bus, wherein the programmable operating parameters used by the microcontroller 420 are stored and modified, as required, in order to customize the operation of IMD 410 to suit the needs of a particular patient. The memory 424 also stores data sets (IN signals, RE signals, raw data, summary data, histograms, etc.), such as pressure data, Sv02 data and the like for a desired period of time (e.g., 1 hour, 24 hours, 1 month). The memory 424 may store instructions to direct the microcontroller 420 to analyze the IN and RE signals and identify characteristics of interest and derive values for predetermined statistical parameters. The pressure, IN and RE data stored in memory 424 may be selectively stored at certain time intervals, such as seconds, minutes to hours periodically or surrounding a particular type of arrhythmia of other irregularity in the heart cycle. For example, the memory 424 may store data for multiple non-consecutive multi-minute intervals.

The stimulation and other operating parameters of the IMD 410 may be non-invasively programmed into the memory 424 through a telemetry circuit 464 in telemetric communication with the external device 104, such as a programmer, trans-telephonic transceiver or a diagnostic system analyzer, or with a bedside monitor 418. The telemetry circuit 464 is activated by the microcontroller 420 by a control signal. The telemetry circuit 464 allows intra-cardiac electrograms, IN data, RE data, pressure data, acoustic data, Sv02 data, and status information relating to the operation of IMD 410 (as contained in the microcontroller 420 or memory 424) to be sent to the external device 104 through an established communication link 468.

The IMD 410 includes a position sensor 465 which operates as discussed herein to generate posture signals that are used to identify an actual posture state of the patient.

The IMD 410 includes an accelerometer or other physiologic sensor 472, commonly referred to as a "rate-responsive" sensor because it is typically used to adjust pacing stimulation rate according to the exercise state of the patient. Optionally, the physiological sensor 472 may further be used to detect changes in cardiac output, changes in the physiological condition of the heart, or changes in activity (e.g., detecting sleep and wake states) and to detect arousal from sleep. While shown as being included within IMD 410, it is to be understood that the physiologic sensor 472 may also be external to IMD 410, yet still be implanted within or carried by the patient. A common type of rate responsive sensor is an activity sensor incorporating an accelerometer or a piezoelectric crystal, which is mounted within the housing 400 of IMD 410.

The IMD 410 may be a passive circuit without a power supply. Optionally, the IMD 410 may include a battery 470, which provides operating power to all of the circuits shown. The IMD 410 is shown as having impedance measuring circuit 430 which is enabled by the microcontroller 420 via a control signal. Herein, impedance is detected for use in sensing respiratory effort. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 430 is advantageously coupled to the switch 448 so that impedance at any desired electrode may be obtained.

Generally, in various embodiments, the processing modules described herein should be understood as a processing circuitry module and may include processing circuitry such as one or more field programmable gate array (FPGA), application specific integrated circuit (ASIC), or microprocessor. The processing modules in various embodiments may be configured to execute one or more algorithms to perform functions described herein. The one or more algorithms may include aspects of embodiments disclosed herein, whether or not expressly identified in a flowchart or as a step of a method.

Figure 5A:
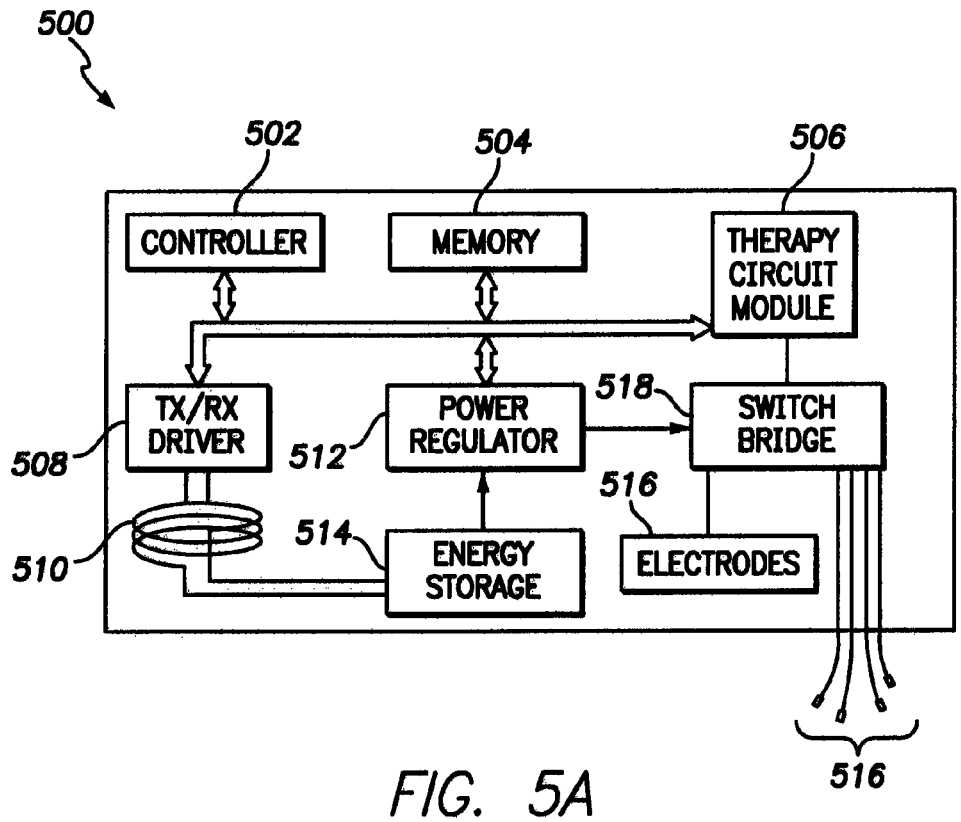
FIG. 5A illustrates a block diagram of an implantable medical device that may operate as one or both of a sensor and for a stimulation device in accordance with an embodiment.

FIG. 5A illustrates a block diagram of an implantable medical device 500 that may operate as one or both of a sensor 102 and/or a stimulation device 110, 112. The device 500 includes a controller 502 that operates as described herein in connection with other embodiments to perform sensing operations, communications operations, analysis of IN and RE signals, control of CSA and OSA therapy, as well as other operations. A memory 504 stores various programming information, firmware, instructions, IN signals, RE signals, baseline information, templates, thresholds and the like. A therapy circuit module 506 controls operation of a switch bridge 518 to connect/disconnect select combinations of electrodes 516 in connection with sensing IN/RE signals and delivering CSA and OSA therapies. The electrodes 516 may be built into a housing of the device 500 or located separate from the housing on one or more leads.

An antenna 510 is configured to receive energy from an external antenna (e.g., antenna 106 and 108) that is provided to an energy storage 514. The energy received by the antenna 510 and stored in energy storage 514 is used to power the electronics within the device 500, as well as to provide energy to deliver CSA and OSA therapies. The energy storage 514 may represent a rechargeable battery, one or more capacitors and other devices capable of storing energy for select periods of time (e.g., for a few seconds during a sensing and therapy delivery session, for several hours over the course of an evening sleep, or for several days).

A power regulator 512 controls an amount of power delivered from the energy storage 514 to the electronic components (e.g., the controller 502, circuit module 506, Tx/Rx driver 508, memory 504), also referred to as circuit operating power. For example, when the electronic components operate at 5V, the power regulator 512 maintains a voltage output from the energy storage 514 at 5V to the electronic components. The power regulator 512 also manages an amount of stimulation energy delivered from the electrodes 516 as CSA and OSA therapy. For example, when stimulation energy level is to be a series of pulses between 5-500 mV or between 5 and 25 mV, the power regulator 512 outputs stimulation power at the requisite voltage level to the switch bridge 518. The therapy circuit module 506 manages switching operations of the switch 518 to form a select number, duration and shape of stimulation pulses.

A Tx/Rx driver 508 manages data communication to and from the device 500 through the antenna 510. For example, the device 500 may send IN/RE signals (analog or digital) through the Tx/Rx driver 508 and antenna 510 to the external device 104. The device 500 may transmit status information, IN signals, RE signals, and the like through the antenna 510 to the external device 104. The device 500 may receive command instructions from the external device 104, such as the type of OSA or CSA therapy to deliver, a mode of operation for the device 500, and the like.

Figure 5B:
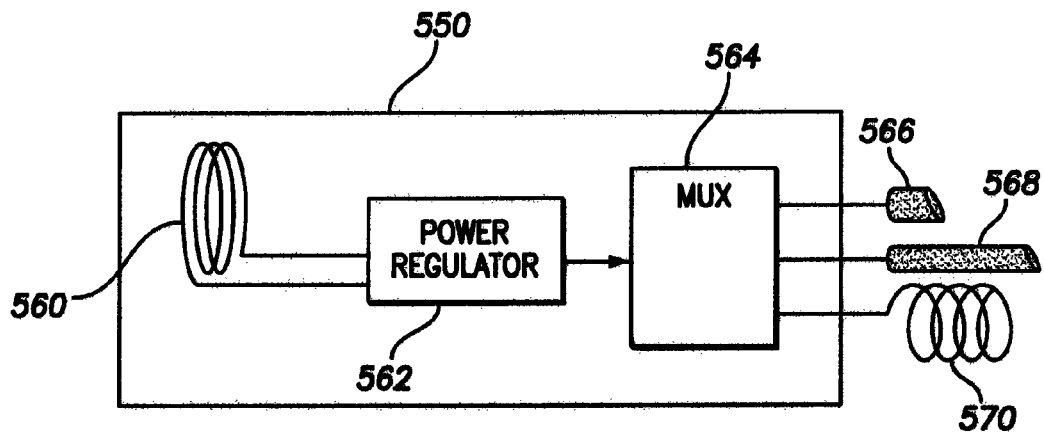
FIG. 5B illustrates a block diagram of an implanted sensor that may operate as a sensor and/or stimulation device in accordance with an embodiment.

FIG. 5B illustrates a block diagram of a simple implanted sensor 550 that may operate as a sensor 102 and/or stimulation device 110, 112. A multiplexer 564 is configured to connect/disconnect select combinations of electrodes 566, 568, 570 in connection with sensing IN/RE signals and delivering CSA and OSA therapies. An antenna 560 is configured to receive energy from an external antenna (e.g., antenna 106 and 108). The received energy is provided directly to a power regulator (or optionally, may be temporarily provided to an energy storage). The energy received by the antenna 560 is used to perform sensing and to provide energy to deliver CSA and OSA therapies. The power regulator 562 manages an amount of stimulation energy delivered from the electrodes 516 as CSA and OSA therapy. The MUX 564 performs switching operations to form a select number, duration and shape of stimulation pulses.

External Device

Figure 6:
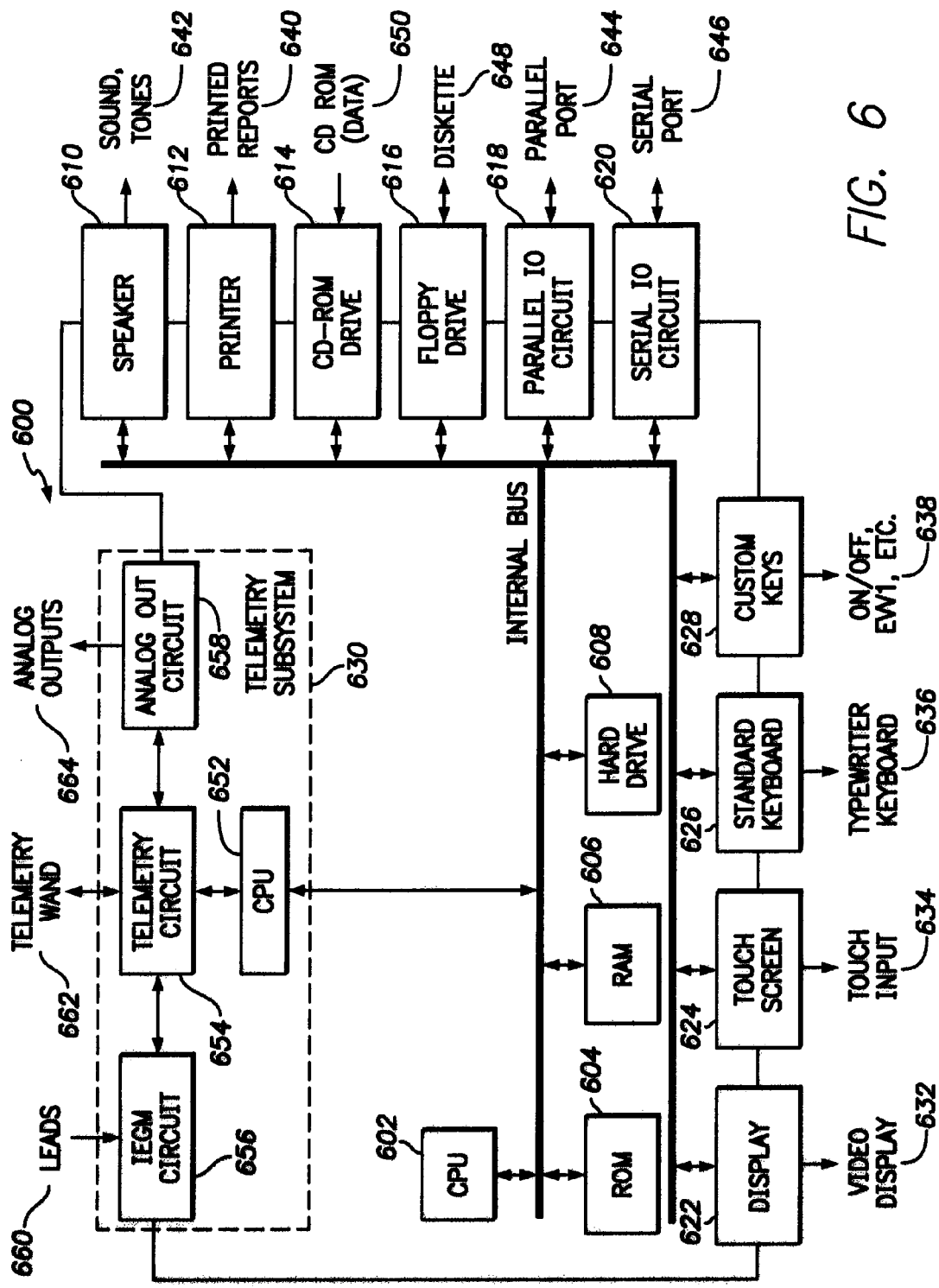
FIG. 6 illustrates a functional block diagram of an external device formed in accordance with an embodiment.

FIG. 6 illustrates a functional block diagram of the external device 600 (which may represent external device 104) that is operated in accordance with the processes described herein and to interface with sensors 102, devices 110, 112 and other implantable medical devices as described herein. The external device 600 may be a workstation, a portable computer, an IMD programmer, a PDA, a cell phone and the like. The external device 600 includes an internal bus that connects/interfaces with a Central Processing Unit (CPU) 602, ROM 604, RAM 606, a hard drive 608, the speaker 610, a printer 612, a CD-ROM drive 614, a floppy drive 616, a parallel I/O circuit 618, a serial I/O circuit 620, the display 622, a touch screen 624, a standard keyboard connection 626, custom keys 628, and a telemetry subsystem 630. The internal bus is an address/data bus that transfers information between the various components described herein. The hard drive 608 may store operational programs as well as data, such as waveform templates and detection thresholds.

The CPU 602 typically includes a microprocessor, a microcontroller, or equivalent control circuitry, designed specifically to control interfacing with the external device 600 and with the DEVICE 110, 112. The CPU 602 performs the COI measurement process discussed above. The CPU 602 may include RAM or ROM memory, logic and timing circuitry, state machine circuitry, and I/O circuitry to interface with the DEVICE 110, 112. The display 622 (e.g., may be connected to the video display 632). The touch screen 624 may display graphic information relating to the DEVICE 110, 112. The display 622 displays various information related to the processes described herein. The touch screen 624 accepts a user's touch input 634 when selections are made. The keyboard 626 (e.g., a typewriter keyboard 636) allows the user to enter data to the displayed fields, as well as interface with the telemetry subsystem 630. Furthermore, custom keys 628 turn on/off 638 (e.g., EVVI) the external device 600. The printer 612 prints copies of reports 640 for a physician to review or to be placed in a patient file, and speaker 610 provides an audible warning (e.g., sounds and tones 642) to the user. The parallel I/O circuit 618 interfaces with a parallel port 644. The serial I/O circuit 620 interfaces with a serial port 646. The floppy drive 616 accepts diskettes 648. Optionally, the floppy drive 616 may include a USB port or other interface capable of communicating with a USB device such as a memory stick. The CD-ROM drive 614 accepts CD ROMs 650.

The telemetry subsystem 630 includes a central processing unit (CPU) 652 in electrical communication with a telemetry circuit 654, which communicates with both an IEGM circuit 656 and an analog out circuit 658. The circuit 656 may be connected to leads 660. The circuit 656 is also connected to the implantable leads to receive and process IEGM cardiac signals as discussed above. Optionally, the IEGM cardiac signals sensed by the leads may be collected by the DEVICE 110, 112 and then transmitted, to the external device 600, wirelessly to the telemetry subsystem 630 input.

The telemetry circuit 654 is connected to a telemetry wand 662. The analog out circuit 658 includes communication circuits to communicate with analog outputs 664. The external device 600 may wirelessly communicate with the DEVICE 110, 112 and utilize protocols, such as Bluetooth, GSM, infrared wireless LANs, HIPERLAN, 3G, satellite, as well as circuit and packet data protocols, and the like. Alternatively, a hard-wired connection may be used to connect the external device 600 to the DEVICE 110, 112.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A method for treating sleep apnea using an implantable device, the method comprising:
    sensing an inspiration (IN) signal representative of inspiration experienced by a patient from a respiratory surrogate signal;
    sensing a respiratory effort (RE) signal representative of an amount of effort exerted by the patient during respiration;
    analyzing the inspiration signal relative to an IN baseline, that corresponds to normal respiratory behavior;
    analyzing the RE signal relative to an RE baseline, that corresponds to a normal amount of respiratory effort exerted by the patient;
    declaring a central sleep apnea (CSA) state when the inspiration signal is less than the IN baseline and the RE signal is less than the RE baseline or an obstructive sleep apnea (OSA) state when the when the inspiration signal is less than the IN baseline and the RE signal is greater than the RE baseline; and
    delivering at least one of a CSA therapy when the CSA state is declared or an OSA therapy when the OSA state is declared.

2. The method of claim 1, wherein the delivering includes delivering at least one of a nerve stimulation or a muscle stimulation configured to induce breathing.

3. The method of claim 1, wherein the CSA therapy includes targeting nerve stimulation at a phrenic nerve when the declaring declares the CSA state.

4. The method of claim 1, wherein the OSA therapy includes targeting nerve stimulation at a hypoglossal nerve when the declaring declares the OSA state.

5. The method of claim 1, wherein the CSA therapy includes targeting muscle stimulation at a diaphragm when the declaring declares the CSA state.

6. The method of claim 1, wherein the OSA therapy includes targeting muscle stimulation at oropharyngeal muscles when the declaring declares the OSA state.

7. The method of claim 1, wherein the sensing includes sensing at least one of a blood pressure or a blood oxygen saturation as an indirect measure of respiration.

8. The method of claim 7, wherein the therapy is delivered upon detection of a change or cessation of respiratory-related blood pressure oscillations in a pulmonary artery.

9. The method of claim 7, wherein the therapy is delivered upon detection of reduced oxygen saturation in a pulmonary arterial blood or superior vena cava.

10. The method of claim 1, wherein the sensing comprises receiving a surrogate pulmonary artery blood pressure (PABP) signal that changes over respiratory cycles, the surrogate PABP signal including an indication of a magnitude and a period of the inspiration.

11. The method of claim 1, wherein the sensing further comprises low pass filtering the PABP signal with a cutoff at a predefined frequency to generate a low pass filtered PABP signal that increases and decreases in magnitude in accordance with changes in inspiration over a respiratory cycle.

12. A system for treating sleep apnea, comprising:
    sensors configured to sense inspiration and output an inspiration (IN) signal, representative of inspiration experienced by a patient, as a respiratory surrogate signal, the sensors further configured to sense a respiratory effort (RE) and output an RE signal representative of an amount of effort exerted by the patient during respiration;
    an analysis circuit module configured to analyze the IN signals relative to an IN baseline, that corresponds to normal respiratory behavior;
    the analysis circuit module configured to analyze the RE signal relative to an RE baseline, that corresponds to a normal amount of respiratory effort exerted by the patient;
    a therapy circuit module configured to declare a central sleep apnea (CSA) state when the inspiration signal is less than the IN baseline and the RE signal is less than the RE baseline or an obstructive sleep apnea (OSA) state when the inspiration signal is less than the IN baseline and the RE signal is greater than the RE baseline; and
    an implantable device configured to deliver at least one of a CSA therapy when the CSA state is declared or an OSA therapy when the OSA state is declared.

13. The system of claim 12, wherein the implantable device includes a lead positioned proximate to nerves or muscle of interest, the lead having electrode configured to deliver at least one of a nerve stimulation or a muscle stimulation configured to induce breathing.

14. The system of claim 12, wherein the therapy circuit module targets nerve stimulation at a phrenic nerve when the declaring declares the CSA state.

15. The system of claim 12, wherein the therapy circuit module targets nerve stimulation at a hypoglossal nerve when the declaring declares the OSA state.

16. The system of claim 12, wherein the therapy circuit module targets muscle stimulation at a diaphragm when the declaring declares the CSA state.

17. The system of claim 12, wherein the therapy circuit module targets muscle stimulation at oropharyngeal muscles when the declaring declares the OSA state.

18. The system of claim 12, wherein the sensors further comprise at least one of an implantable blood pressure sensor or an implantable blood oxygen saturation sensor configured to generate the IN signal as the respiratory surrogate signal.

19. The system of claim 12, wherein the sensors include a pulmonary pressure sensor configured to output a pulmonary artery blood pressure (PABP) signal as the IN signal, further comprising a low pass filter configured to remove a high frequency component from the PABP signal to produce a lowpass PABP signal as the IN signal.

20. The system of claim 12, wherein the analysis circuit module is configured to receive, as the IN signal, a surrogate positive airway pressure (PABP) signal that changes over respiratory cycles, the analysis circuit module configured to declare the CSA state or OSA state when at least one of a peak to peak magnitude or a period of the inspiration fails to satisfy at least one of a predetermined inspiration magnitude or period thresholds.

21. The system of claim 12, wherein the sensors further comprise a galvanic sensor configured to sense the RE signal representative of the amount of effort exerted by the patient during respiration.

22. The system of claim 12, further comprising an external device that includes the analysis and therapy circuit modules, the external device having inputs configured to receive the IN and RE signals from the sensors, the external device coupled to an antenna configured to communicate with the implantable device.

23. The system of claim 12, further comprising an external device that includes the analysis and therapy circuit modules, wherein the sensors are implantable in the patient, the external device coupled to an antenna configured to communicate with the sensors to receive at least one of the IN or RE signals.

24. The system of claim 12, further comprising first and second antenna are configured to be located in a bed or pillow of the patient proximate to a torso and head of the patient.

\* \* \* \* \*